United States Patent [19]
Wakimura et al.

[11] Patent Number: 5,689,011
[45] Date of Patent: Nov. 18, 1997

[54] PROCESS FOR THE PRODUCTION OF GLYOXALS AND CATALYSTS THEREFOR

[75] Inventors: Kazuo Wakimura, Sennan; Kazuhuyu Sudoh, Yokohama; Masao Tanaka; Hatuo Inoue, both of Sakai; Nobuhisa Iwane, Takaishi, all of Japan

[73] Assignee: Mitsui Toatsu Chemicals, Inc., Tokyo, Japan

[21] Appl. No.: 443,665

[22] Filed: May 18, 1995

[30] Foreign Application Priority Data

May 30, 1994 [JP] Japan ................................. 6-116980

[51] Int. Cl.$^6$ ........................................ C07C 45/00
[52] U.S. Cl. ................................ 568/486; 568/404
[58] Field of Search ............................. 568/404, 486

[56] References Cited

U.S. PATENT DOCUMENTS

| | | | |
|---|---|---|---|
| 3,948,997 | 4/1976 | Howe et al. | 260/596 |
| 4,503,261 | 3/1985 | Sauer et al. | |

FOREIGN PATENT DOCUMENTS 0597454  5/1994  European Pat. Off. .

*Primary Examiner*—Samuel Barts
*Attorney, Agent, or Firm*—Burns, Doane, Swecker & Mathis

[57] ABSTRACT

The present invention provides a process for the production of glyoxals which comprises effecting the oxidative dehydrogenation of a glycol at a temperature of 400° to 700° C. in the presence of a silver-based catalyst composed of silver and at least one element selected from the group consisting of gold, platinum, rhodium and palladium, and phosphorus or a phosphorus compound, as well as such catalysts. These process and catalysts make it possible to produce high-quality glyoxals in high yield and with industrial advantages while minimizing the contents of unreacted raw material and reaction intermediates such as glycolaldehyde and acetol.

10 Claims, No Drawings

PROCESS FOR THE PRODUCTION OF GLYOXALS AND CATALYSTS THEREFOR

BACKGROUND OF THE INVENTION

1. Field of the Invention

This invention relates to a novel process for the production of glyoxals and catalysts therefor. More particularly, it relates to a process for the production of glyoxals by the vapor-phase oxidative dehydrogenation reaction of glycols with the aid of a specific catalyst and to such catalysts.

2. Description of the Related Art

Glyoxals are compounds which are very useful as textile processing aids, paper processing aids, soil stabilizers and intermediates in organic syntheses, and a variety of processes for the production of glyoxals by oxidative dehydrogenation of glycols have been proposed.

Examples of such processes include a process using a catalyst composed of Cu and/or Ag and phosphorus (Japanese Patent Publication No. 1364/'73), a process involving oxidation in the presence of silver crystals having a definite particle size (0.1 to 2.5 mm) (Japanese Patent Publication No. 54011/'86), a process involving oxidation by contact with silver crystals in the presence of a vaporizable phosphorus compound (Japanese Patent Publication No. 49292/'90), a process for the production of diketones by use of a catalyst comprising Ag crystals and/or Cu crystals having a definite particle diameter of 0.1 to 2.5 mm (Japanese Patent Publication No. 56214/'88), a process for the production of methylglyoxal by use of a catalyst comprising Ag crystals having a particle diameter of 0.1 mm or less (Japanese Patent Publication No. 40336/'92), and a process for the production of diketones by use of a catalyst containing Cu or Ag as disclosed in Japanese Patent Laid-Open No. 156739/'88, or a catalyst containing Cu and Ag as disclosed in Japanese Patent Laid-Open No. 258829/'88.

Moreover, several processes for producing dialdehydes with the aid of a silver catalyst supported on a carrier have also been proposed. For example, in Izv. Akad. Nauk. SSSR, Ser. Khim., 641–643(1964), reaction was carried out at a temperature of 600° C. in the presence of an alumina-supported silver catalyst (with an Ag content of 32%). However, only poor results (i.e., a yield of 20% and a space time yield of 23.8 kg-GX/m$^3$-cat-hr) were obtained. Other processes are disclosed in Japanese Patent Publication No. 4816/'88 and the like, but these processes have the disadvantage that diluted ethylene glycol is used and that the product has a high content of unreacted ethylene glycol. In addition, a process using a catalyst comprising silver oxide and zinc oxide is disclosed in Japanese Patent Publication No. 10570/'78. Thus, there are a number of well-known processes for producing a dialdehyde by oxidative dehydrogenation of ethylene glycol in the presence of a copper catalyst or a silver catalyst.

For example, where glyoxal and methylglyoxal are used as textile processing aids or paper processing aids, a high content of impurities such as glycolaldehyde and acetol is undesirable in that they may cause yellowing and other problems. Moreover, where glyoxal and methylglyoxal are used as intermediate materials for the manufacture of dyes, drugs, perfumes and the like, a high content of impurities such as acetol is undesirable in that they may induce side reactions and the like. Thus, it is necessary to minimize such impurities.

Since it is difficult to separate or remove any unreacted raw material (i.e., ethylene glycol or propanediol) and reaction intermediates (e.g., glycolaldehyde or acetol) from the resulting aqueous solution of the product (i.e., glyoxal or methylglyoxal), it is necessary that no raw martial (i.e., ethylene glycol or propanediol) be left and no reaction intermediates (e.g., glycolaldehyde or acetol) be formed in the oxidative dehydrogenation step. Consequently, strict manufacturing conditions and an appropriate catalyst have been chosen so as to decrease impurities at the expense of yield.

Moreover, since particulate silver used as a catalyst is expensive, silver is recovered from the spent catalyst and reused. The silver can be regenerated, for example, by dissolving the spent catalyst in nitric acid, concentrating the solution to crystallize silver nitrate, recovering silver nitrate crystals, and electrolyzing a solution of the silver nitrate, or by carrying out electrolysis in an electrolytic solution while using the spent silver catalyst directly as an electrode, so as to precipitate silver particles. The silver thus obtained is used as a catalyst for industrial purposes.

However, when a silver catalyst which has been used for a long period of time and consolidated into a mass is regenerated repeatedly, the content of impurities such as unreacted raw material and reaction intermediates is increased, thus posing a serious problem in the preparation of silver catalysts. Moreover, when supported catalysts prepared in different lots or on different scales are used, the content of impurities such as glycolaldehyde and acetol may be increased, even if the raw material is reacted under the same conditions. Thus, it has been difficult to prepare catalysts having good reproducibility.

For example, in Japanese Patent Publication No. 1364/'73, the feed rate of ethylene glycol or 1,2-propanediol (1.333 g-propanediol/cm$^3$-cat-hr) was severely limited, so that the conversion of 1,2-propanediol (93%) and the space time yield of methylglyocal were low and the yield of acetol (7%) was high.

Japanese Patent Laid-Open No. 59933/'83 discloses a process for oxidizing glycols by contact with a phosphorus-containing silver catalyst in the presence of a vaporizable phosphorus compound. In Example 1 of this patent, a glyoxal yield of 80% was maintained for 11 days by reacting a mixture of ethylene glycol and ammonium primary phosphate in the presence of a catalyst comprising particulate silver having ammonium phosphate added thereto. However, this process still suffers from a low space time yield.

According to a process described in Japanese Patent Publication No. 54011/'86, a high yield of glyoxal (55–66.4%) and a high space time yield (9.4–14.6 g-glyoxal/cm$^3$-cat-hr) were achieved. However, the conversion was as low as 97.8–98%. Since unreacted ethylene glycol which cannot be easily separated from glyoxal remains and mixes in the desired glyoxal, this is not a satisfactory process for producing high-quality products on an industrial scale.

U.S. Pat. No. 4,555,583 (corresponding to Japanese Patent Publication No. 49292/'90) discloses a process for oxidizing ethylene glycol by contact with silver crystals in the presence of a vaporizable phosphorus compound. In Example 2 of this patent, an ethylene glycol conversion of 100%, a selectivity for glyoxal of 80.4% and a selectivity for glycolaldehyde of 1.3% were obtained by carrying out reaction at a temperature of 501° C. Although the yield of glyoxal is high, this process still has the disadvantage that the content of glycolaldehyde as an impurity is unduly high. The formation of glycolaldehyde can be minimized by use of a catalyst comprising fine silver particles (Example 1), but this undesirably increases the pressure loss of the catalyst bed.

In Japanese Patent Publication No. 40336/'92, there were obtained good results including a conversion of 99.9%, a yield of 63.8–66.1%, a catalyst load of 3.33 g-propylene glycol/g-cat-hr and a space time yield of 2.09 g-methylglyoxal/g-cat-hr. However, no mention is made of impurities such as acetol. This process has the disadvantage that the fine silver particles used as the catalyst increase the pressure loss of the catalyst bed. Moreover, it is also disadvantageous that fine silver particles cannot be obtained in high yield even by electrolysis of an aqueous solution of silver nitrate or by vacuum deposition.

In Japanese Patent Publication No. 56214/'88, a conversion of 100–95%, a yield of 84.2–76%, a catalyst load of 0.8–1.6 tons/m²-cat-hr and a space time yield of 33.4–57 g/cm³-cat-hr were obtained in the oxidation of n-hexanediol-2,5 or 2,3-butanediol. However, the yields of reaction intermediates such as hexanol-2-one-5 (2.8%, 8.5%) and butan-3-ol-2-one (7.1%) were high. Moreover, the production of glyoxal and methylglyoxal is not specifically described therein.

Examples of the production of glyoxal are disclosed in Japanese Patent Laid-Open Nos. 156739/'88 and 258829/'88. In the example of the production of glyoxal which is disclosed in Japanese Patent Laid-Open No. 156739/'88, the yield of glyoxal (77.1%) was high, but the conversion of the raw material (94.2%) and the space time yield of the product (0.092 g-glyoxal/cm³-cat-hr) were low. Similarly, in the example of the production of glyoxal which is disclosed in Japanese Patent Laid-Open No. 258829/'88, the yield of glyoxal (71.5%) was high, but the conversion of the raw material (99%) and the space time yield of the product (0.082 g-glyoxal/cm³-cat-hr) were low. Moreover, no example of the production of methylglyoxal is disclosed therein.

In addition, a variety of processes for producing dialdehydes with the aid of a silver catalyst supported on a carrier have also been proposed. In such catalysts, the content of silver is as low as 5–30 wt. %. For example, in Izv. Akad. Nauk. SSSR, Ser. Khim., 641–643(1964), reaction was carried out at a temperature of 600° C. in the presence of an alumina-supported silver catalyst (with an Ag content of 32 wt. %). However, only poor results (i.e., a yield of 20% and a space time yield of 23.8 kg-glyoxal/m³-cat-hr) were obtained. In Example 2 of Japanese Patent Publication No. 4816/'88, reaction was carried out at a temperature of 400° C. in the presence of an alumina-supported silver catalyst (with an Ag content of 10 wt. %), and a conversion of 98%, a selectivity of 65% and a space time yield of 120 kg-glyoxal/m³-cat-hr were obtained. However, this process cannot be regarded as satisfactory because of its low space time yield.

In Example 3 of Japanese Patent Laid-Open No. 38227/'83, an ethylene glycol conversion of 97% and a selectivity of 74% were obtained by use of a silver catalyst (with an Ag content of 8 wt. %) comprising silver supported on silicon carbide and containing ammonium phosphate in an amount of 200 ppm as phosphorus. However, the space time yield was as low as 0.26 kg-glyoxal/m³-cat-hr. In Example 3 of Japanese Patent Laid-Open No. 156739/'88, a conversion of 92.1%, a selectivity of 67%, a glycolaldehyde yield of 2.7% and a space time yield of 40 kg-glyoxal/m³-cat-hr were obtained by carrying out reaction at a temperature of 360° C. in the presence of a catalyst comprising silver-coated steatite spherules. Although the yield is high, this process has the disadvantage that the product contains considerable amounts of unreacted ethylene glycol and glycolaldehyde and that the space time yield is low.

Furthermore, in Journal of Catalysis, 142, 729–734 1993), a conversion of 98.5%, a selectivity of 73% and a space time yield of 920 kg-glyoxal/m³-cat-hr were obtained by carrying out reaction at a temperature of 550° C. in the presence of a silicon carbide-supported silver catalyst (with an Ag content of 5 or 8 wt. %). However, this process has the disadvantage that the product contains a considerable amount of unreacted ethylene glycol and that the space time yield is low.

In Japanese Patent Publication No. 10570/'78, a relatively high space time yield of methylglyoxal (i.e., 1,768–8,071 g-methylglyoxal/liter-cat-hr) was achieved by use of a catalyst comprising silver oxide and zinc oxide supported on silica or alumina. However, this process is still unsatisfactory in that the conversion of 1,2-propanediol (96.3–86.9%) was low and the content of impurities such as acetol (5.0–11.3%) was high. It is also described therein that, in a comparative example using a catalyst comprising 40 wt. % of silver supported on alumina sol, the reaction yield (48.4%) and the space time yield (1.3 g-methylglyoxal/cm³-cat-hr) were low and the contents of impurities such as acetol (2.4%) and acetaldehyde (8.2%) were high.

Thus, there has not yet been developed a silver catalyst which is useful in the practical production of glyoxals and can achieve a high conversion, a high selectivity and a high space time yield while minimizing the content of impurities.

SUMMARY OF THE INVENTION

It is an object of the present invention to provide a process for the production of glyoxals which can achieve a high conversion, a high selectivity and a high space time yield while minimizing the content of impurities.

It is another object of the present invention to provide novel catalysts which can be used in this process.

The present inventors repeated intensive investigations in order to overcome the disadvantages of prior art processes for the production of glyoxals by vapor-phase oxidation of glycols, and have now completed the present invention.

According to the present invention, there is provided a process for the production of glyoxals which comprises effecting the oxidative dehydrogenation of a glycol at a temperature of 400° to 700° C. in the presence of a silver-based catalyst composed of silver and at least one element selected from the group consisting of gold, platinum, rhodium and palladium, and phosphorus or a phosphorus compound.

When the process of the present invention is employed to produce glyoxals from the corresponding glycols (e.g., 1,2-propanediol and ethylene glycol), the amount of silver used can be reduced, the useful life of the catalyst can be prolonged, the stability of the vapor-phase dehydrogenation reaction can be improved, and the degree of conversion of the raw material can be enhanced. Thus, glyoxals such as methylglyoxal and glyoxal can be produced in high yield so as to bring about very great industrial advantages.

DETAILED DESCRIPTION OF THE PREFERRED EMBODIMENTS

The present invention will be more specifically described hereinbelow.

The glycols which can be used as raw materials in the present invention are defined as compounds of the following formula (I):

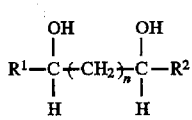

(I)

where n is a whole number of 0 to 10, preferably 0 or 1, and $R^1$ and $R^2$ are hydrogen atoms or alkyl groups, preferably hydrogen atoms or methyl groups, and may be the same or different.

The glyoxals which are desired products in the present invention can be represented by the following formula (II):

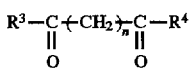

(II)

where n is a whole number of 0 to 10, preferably 0 or 1, and $R^3$ and $R^4$ are hydrogen atoms or alkyl groups, preferably hydrogen atoms or methyl groups, and may be the same or different.

The silver-based catalyst used in the present invention is composed of silver, which constitutes the principal component thereof and is used as such or in the form of a supported silver catalyst, and at least one element selected from the group consisting of gold, platinum, rhodium and palladium. As the silver catalyst, there may be used crystalline silver particles obtained, for example, by electrolysis of an aqueous solution of silver nitrate, shavings of metallic silver, silver particles obtained by spraying and quenching molten silver, or supported silver.

No particular limitation is placed on the catalyst carrier used in the present invention, and there may be chosen any material that is usually used as a catalyst carrier. However, it is preferable to use a material which has essentially no catalytic activity in itself and is characterized by a relatively small specific surface area and a relatively small particle diameter. The materials useful as carriers include, for example, oxides, nitrides, carbides and intermediate compositions thereof, as well as other inert inorganic compounds. Of these materials, silica, alumina, zirconia, silicon nitride and silicon carbide having, for example, a specific surface area of 5 m²/g or less, preferably 0.01 to 2.0 m²/g, and a particle diameter of 25 to 1,000 μm, preferably 50 to 500 μm, are especially preferred. In order to prepare a supported catalyst, such a carrier is impregnated with an aqueous solution of a silver compound and then subjected to a series of operations including mixing, drying, firing, grinding and classification. This procedure is repeated until a supported catalyst having a desired silver content is obtained.

The amount of silver supported is preferably in the range of 50 to 95 wt. % based on the combined weight of the silver and the inert carrier.

The at least one element selected from the group consisting of gold, platinum, rhodium and palladium is preferably added in an amount, as expressed on an elemental basis, of 0.001 to 10 wt. %, more preferably 0.01 to 5 wt. % and most preferably 0.01 to 2 wt. %, based on the silver. As to the method of addition, the element to be added may be melted together with silver. The resulting product can be used in the form of wire or shavings made of the solidified melt or in the form of particles obtained by spraying and quenching the melt. Alternatively, these elements may be added to and supported on a silver catalyst by impregnating the silver catalyst with an aqueous solution of at least one compound of gold, platinum, rhodium or palladium and then subjecting the impregnated silver catalyst to a series of operations including mixing, drying, firing, grinding and classification. These metallic elements are preferably used in such a form as to coat the silver partially.

A desired catalyst can be obtained by suspending a silver catalyst (such as electrolytic silver or supported silver) in an aqueous solution of at least one compound of gold, platinum, rhodium or palladium, rendering the suspension alkaline with ammonia or the like, and reducing the silver catalyst with the aid of a reducing agent (such as formalin or hydrazine) or flowing hydrogen gas. When the silver-based catalyst is heat-treated at a temperature of 200° to 700° C. in a reducing atmosphere or an atmosphere of an inert gas prior to its use for the oxidative dehydroganation reaction, more preferable results can be obtained.

In the present invention, the addition of such an element to a silver catalyst can reduce the contents of unreacted raw material and reaction intermediates such as glycolaldehyde, acetol and acetaldehyde. Moreover, this makes it possible to achieve a high conversion of glycols such as ethylene glycol and 1,2-propanediol and a high selectivity for glyoxals such as glyoxal and methylglyoxal, while maintaining a long useful life of the catalyst.

The process of the present invention is based on an oxidative dehydrogenation reaction carried out with the aid of molecular oxygen. Although either pure oxygen or air may be used as the molecular oxygen, the latter is preferred from an economic point of view. In order to obtain the desired glyoxal in high yield, the glycol and the molecular oxygen are reacted under dilution with an inert gas. As the inert gas, there may used nitrogen, a rare gas (such as helium or argon), carbon dioxide or water vapor.

Reaction at lower temperatures tends to increase the contents of unreacted glycol and acetol, while reaction at higher temperatures tends to increase the formation of formalin, carbon monoxide and carbon dioxide. In either case, the yield of the desired glyoxal is decreased. Accordingly, the preferred reaction temperature for the process of the present invention is in the range of 400° to 700° C.

In the present invention, phosphorus or a phosphorus compound may be used for the reaction by mixing a predetermined amount thereof with the raw material in advance or by providing it, as such or as a solution, separately from the raw material and adding it to the reaction system. The phosphorus or phosphorus compound is usually added in an amount of 0.05 to 10 ppm, as phosphorus, based on the glycol used as the raw material. As the phosphorus compound, there can be effectively used any of various organic phosphorus compounds including primary, secondary and tertiary phosphines (such as mono-, di- and trimethylphosphines), phosphorous esters (such as methyl phosphite and ethyl phosphite), dimethyl methylphosphonate, diethyl ethylphosphonate and the like.

However, phosphorus compounds having high boiling points are undesirable because they create the necessity of raising the temperature of the evaporator to an undue extent and because they may stay, decompose and accumulate in the evaporator to corrode the material of the equipment and the iron rust so formed may migrate to the reaction bed and affect the reaction. Consequently, organic phosphorus compounds having relatively low boiling points, such as methyl phosphite, ethyl phosphite, methyl phosphate and ethyl phosphate, are more preferably used. The addition of such phosphorus compounds significantly suppresses the formation of oxidation products (such as carbon monoxide and carbon dioxide) and decomposition products (such as formaldehyde), as compared with the case where they are not added. As a result, the yield of the desired product such as glyoxal or methylglyoxal is markedly improved.

The present invention is further illustrated by the following examples. However, these examples are not to be construed to limit the invention.

EXAMPLE 1

(Preparation of catalysts)

a) Of particulate silver obtained by electrolysis, 50 g of particulate silver having particle sizes of 500 to 105 μm was soaked in 500 ml of an aqueous solution of chloroplatinic acid containing 0.005 wt. % of platinum based on the silver. 50 ml of 37% formalin was added thereto with stirring, and the pH of the solution was then adjusted to 10 by the addition of aqueous ammonia. Reduction by formalin was carried out at 50° C. for 2 hours, followed by filtration, water washing and drying. The resulting catalyst was called "catalyst A".

b) Of particulate silver obtained by electrolysis, 50 g of particulate silver having particle sizes of 500 to 105 μm was soaked in an aqueous solution of chloroplatinic acid containing 0.05 wt. % of platinum based on the silver. Then, reduction by formalin was carried out in the same manner as for catalyst A. The resulting catalyst was called "catalyst B".

c) Of particulate silver obtained by electrolysis, 50 g of particulate silver having particle sizes of 500 to 105 μm was soaked in an aqueous solution of chloroplatinic acid containing 0.5 wt. % of platinum based on the silver. Then, reduction by formalin was carried out in the same manner as for catalyst A. The resulting catalyst was called "catalyst C".

d) Of particulate silver obtained by electrolysis, 50 g of particulate silver having particle sizes of 500 to 105 μm was soaked in an aqueous solution of chloroauric acid containing 0.2 wt. % of gold based on the silver. Then, reduction by formalin was carried out in the same manner as for catalyst A. The resulting catalyst was called "catalyst D".

e) Of particulate silver obtained by electrolysis, 50 g of particulate silver having particle sizes of 500 to 105 μm was soaked in an aqueous solution of rhodium chloride containing 0.2 wt. % of rhodium based on the silver. Then, reduction by formalin was carried out in the same manner as for catalyst A. The resulting catalyst was called "catalyst E".

f) Of particulate silver obtained by electrolysis, 50 g of particulate silver having particle sizes of 500 to 105 μm was soaked in an aqueous nitric acid solution of dinitrodiaminepalladium containing 0.2 wt. % of palladium based on the silver. Then, reduction by formalin was carried out in the same manner as for catalyst A. The resulting catalyst was called "catalyst F".

(Reaction)

For each of the above-described particulate catalysts, a stainless steel reactor having an inner diameter of 27.4 mm was packed with 6 ml of a fraction having particle sizes of 500 to 250 μm so as to form the lowermost catalyst layer. Then, 5 ml of a fraction having particle sizes of 250 to 150 μm was placed on the lowermost catalyst layer and, further, 4 ml of a fraction having particle sizes of 150 to 105 μm was placed as the uppermost catalyst layer.

To the reactor packed in the above-described manner were fed 1,2-propanediol containing trimethyl phosphite in an amount of 3 ppm, as phosphorus, based on the 1,2-propanediol at a rate of 125 g/hr, water at a rate of 125 g/hr, air at a rate of 190 liters/hr, and nitrogen at a rate of 500 liters/hr. These components were fed through an evaporator and a preheater so as to form a descending flow. After the reaction was continued at a predetermined temperature for 10 days, the reaction gas was cooled and the product was collected by separation in an absorption column using water as absorbent. The results of the reactions are shown in Table 1.

EXAMPLE 2

In the same manner as in Example 1, a stainless steel reactor having an inner diameter of 27.4 mm was packed with catalyst D so as to form three layers having different particle sizes. Then, hydrogen gas was passed therethrough at 400° C. for an hour to reduce the catalyst. Thereafter, reaction was carried out by passing a reaction gas through the reactor in the same manner as in Example 1. The results of the reaction are shown in Table 1.

COMPARATIVE EXAMPLE 1

In the same manner as in Example 1, a stainless steel reactor having an inner diameter of 27.4 mm was packed with particulate silver obtained by electrolysis so as to form three layers having different particle sizes. Then, reaction was carried out by passing a reaction gas through the reactor in the same manner as in Example 1. The results of the reaction are shown in Table 1.

COMPARATIVE EXAMPLE 2

In the same manner as in Example 1, a stainless steel reactor having an inner diameter of 27.4 mm was packed with each of catalysts A–F so as to form three layers having different particle sizes. Then, reaction was carried out by passing a reaction gas through the reactor in the same manner as in Example 1, except that no phosphorus was added to the reaction gas. The results of the reactions are shown in Table 1.

TABLE 1

|  | Reaction temperature (°C.) | Conversion of PG (%) | Selectivity for MGX (%) | Yield of acetol (%) | Space time yield (g/cm$^3$ · hr) |
| --- | --- | --- | --- | --- | --- |
| Example 1 |  |  |  |  |  |
| Catalyst A | 486 | 99.9 | 62.8 | 5.0 | 4.8 |
| Catalyst B | 490 | 99.9 | 65.9 | 3.4 | 5.0 |
| Catalyst C | 495 | 99.9 | 68.2 | 1.9 | 5.2 |
| Catalyst D | 494 | 99.8 | 67.0 | 2.8 | 5.2 |
| Catalyst E | 492 | 99.9 | 68.5 | 2.9 | 5.3 |
| Catalyst F | 492 | 99.8 | 67.8 | 2.2 | 5.4 |
| Example 2 | 491 | 99.8 | 69.7 | 1.7 | 5.2 |
| Comp. Ex. 1 | 483 | 99.9 | 61.0 | 6.7 | 4.6 |
| Comp. Ex. 2 |  |  |  |  |  |
| Catalyst A | 494 | 99.9 | 54.7 | 6.1 | 3.8 |
| Catalyst B | 498 | 99.9 | 56.3 | 5.7 | 4.1 |
| Catalyst C | 500 | 99.9 | 56.5 | 5.2 | 4.2 |
| Catalyst D | 501 | 99.9 | 55.4 | 4.9 | 4.1 |
| Catalyst E | 498 | 99.9 | 57.1 | 5.5 | 4.4 |
| Catalyst F | 499 | 99.9 | 56.8 | 4.6 | 4.3 |

Note: PG and MGX represent 1,2-propanediol and methylglyoxal, respectively.

EXAMPLE 3

In the same manner as in Example 1, a stainless steel reactor having an inner diameter of 27.4 mm was packed with each of catalysts E and F. To the reactor so packed were fed ethylene glycol containing trimethyl phosphite in an amount of 3 ppm, as phosphorous, based on the ethylene glycol at a rate of 150 g/hr, water at a rate of 150 g/hr, air at a rate of 280 liters/hr, and nitrogen at a rate of 650 liters/hr. These components were fed through an evaporator and a preheater so as to form a descending flow. After the reaction was continued for 10 days, the reaction gas was cooled and the product was collected by separation in an absorption column using water as absorbent. The results of the reactions are shown in Table 2.

COMPARATIVE EXAMPLE 3

In the same manner as in Example 3, a stainless steel reactor having an inner diameter of 27.4 mm was packed with particulate silver obtained by electrolysis so as to form three layers having different particle sizes. Then, reaction was carried out by passing a reaction gas through the reactor in the same manner as in Example 3. The results of the reaction are shown in Table 2.

TABLE 2

|  | Reaction temperature (°C.) | Conversion of EG (%) | Selectivity for GX (%) | Yield of G-CHO (%) | Space time yield (g/cm$^3$ · hr) |
| --- | --- | --- | --- | --- | --- |
| Example 3 |  |  |  |  |  |
| Catalyst E | 599 | 99.8 | 64.3 | 0.20 | 6.3 |
| Catalyst F | 596 | 99.7 | 63.9 | 0.18 | 6.5 |
| Comp. Ex. 3 | 604 | 99.7 | 60.1 | 0.41 | 5.5 |

Note: EG, GX and G-CHO represent ethylene glycol, glyoxal and glycolaldehyde, respectively.

EXAMPLE 4

(Preparation of catalysts)

g) 100 g of silica having a specific surface area of 1.2 m$^2$/g and a particle size distribution comprising 10 wt. % of 400 to 250 μm, 15 wt. % of 250 to 150 μm, 29 wt. % of 150 to 105 μm, 33 wt. % of 105 to 75 μm and 13 wt. % of 75 to 50 μm was impregnated and mixed with 50 g of a silver nitrate solution (prepared from 200 g of silver nitrate and 200 g of water), and then dried at 100° C. with mixing. The resulting dry powder was heat-treated in air at 600° C. for 30 minutes to prepare a supported catalyst having a silver content of 78 wt. %. This supported catalyst was called "catalyst G".

h) 50 g of the aforesaid supported catalyst G was impregnated with an aqueous solution of chloroauric acid containing 0.5 wt. % of gold based on the silver, and then dried at 100° C. with mixing. The resulting dry powder was heat-treated in air at 500° C. for 30 minutes, followed by cooling, grinding and classification. This catalyst was called "catalyst H".

i) 50 g of supported catalyst G was impregnated with an aqueous solution of ammonium chloroplatinate containing 0.5 wt. % of platinum based on the silver, and then dried at 100° C. with mixing. The resulting dry powder was heat-treated in air at 500° C. for 30 minutes, followed by cooling, grinding and classification. This catalyst was called "catalyst I".

j) 50 g of supported catalyst G was impregnated with an aqueous solution of rhodium chloride containing 0.5 wt. % of rhodium based on the silver, and then dried at 100° C. with mixing. The resulting dry powder was heat-treated in air at 500° C. for 30 minutes, followed by cooling, grinding and classification. This catalyst was called "catalyst J".

k) 50 g of supported catalyst G was impregnated with an aqueous solution of palladium nitrate containing 0.5 wt. % of palladium based on the silver, and then dried at 100° C. with mixing. The resulting dry powder was heat-treated in air at 500° C. for 30 minutes, followed by cooling, grinding and classification. This catalyst was called "catalyst K".

(Reaction)

Each of supported catalysts H–K was classified. Then, a stainless steel reactor having an inner diameter of 27.4 mm was packed with 5 ml of a fraction having particle sizes of 500 to 250 μm so as to form the lowermost catalyst layer. Then, 5 ml of a fraction having particle sizes of 250 to 150 μm was placed on the lowermost catalyst layer and, further, 5 ml of a fraction having particle sizes of 150 to 105 μm was placed as the uppermost catalyst layer.

To the reactor packed in the above-described manner were fed ethylene glycol containing trimethyl phosphite in an amount of 3 ppm, as phosphorus, based on the ethylene glycol at a rate of 150 g/hr, water at a rate of 150 g/hr, air at a rate of 280 liters/hr, and nitrogen at a rate of 650 liters/hr. These components were fed through an evaporator and a preheater so as to form a descending flow. After the reaction was continued for 10 days, the reaction gas was cooled and the product was collected by separation in an absorption column using water as absorbent. The results of the reactions are shown in Table 3.

COMPARATIVE EXAMPLE 4

In the same manner as in Example 4, a reactor was packed with supported catalyst G and reaction was carried out. The results of the reaction are shown in Table 3.

COMPARATIVE EXAMPLE 5

A reactor was packed with each of supported catalysts H–K in the same manner as in Example 4. Then, reaction was carried out by passing a reaction gas through the reactor in the same manner as in Example 4, except that no phosphorus was added to the reaction gas. The results of the reactions are shown in Table 3.

TABLE 3

|  | Reaction temperature (°C.) | Conversion of EG (%) | Selectivity for GX (%) | Yield of G-CHO (%) | Space time yield (g/cm$^3$ · hr) |
| --- | --- | --- | --- | --- | --- |
| Example 4 |  |  |  |  |  |
| Catalyst H | 597 | 99.7 | 64.2 | 0.22 | 6.0 |
| Catalyst I | 600 | 99.9 | 65.4 | 0.24 | 6.1 |
| Catalyst J | 601 | 99.7 | 64.9 | 0.21 | 6.1 |
| Catalyst K | 596 | 99.8 | 63.5 | 0.28 | 5.9 |
| Comp. Ex. 4 |  |  |  |  |  |
| Catalyst G | 605 | 99.7 | 61.2 | 0.42 | 5.7 |
| Comp. Ex. 5 |  |  |  |  |  |
| Catalyst H | 608 | 99.8 | 57.4 | 0.20 | 5.3 |
| Catalyst I | 611 | 99.9 | 58.2 | 0.22 | 5.4 |
| Catalyst J | 609 | 99.8 | 57.1 | 0.20 | 5.1 |
| Catalyst K | 608 | 99.7 | 55.9 | 0.25 | 4.7 |

Note: EG, GX and G-CHO represent ethylene glycol, glyoxal and glycolaldehyde, respectively.

EXAMPLE 5

(Preparation of catalysts)

l) 100 g of α-alumina having a specific surface area of 0.13 m$^2$/g and a particle size distribution comprising 14 wt. % of 500 to 250 μm, 30 wt. % of 250 to 150 μm, 32 wt. % of 150 to 105 μm, 16 wt. % of 105 to 75 μm and 8 wt. % of 75 to 50 μm was treated in the same manner as for catalyst G to prepare a supported catalyst having a silver content of 56 wt. %. This supported catalyst was called "catalyst L".

m) 50 g of the aforesaid supported catalyst L was impregnated with an aqueous solution of chloroplatinic acid containing 1.0 wt. % of platinum based on the silver, and then dried at 100° C. with mixing. The resulting dry powder was heat-treated in air at 500° C. for 30 minutes, followed by cooling, grinding and classification. This catalyst was called "catalyst M".

n) 50 g of supported catalyst L was impregnated with an aqueous nitric acid solution of dinitrodiamminepalladium containing 1.0 wt. % of palladium based on the silver, and then dried at 100° C. with mixing. The resulting dry powder was heat-treated in air at 500° C. for 30 minutes, followed by cooling, grinding and classification. This catalyst was called "catalyst N".

o) 50 g of supported catalyst L was impregnated with an aqueous solution of chloroplatinic acid containing 1.0 wt. % of platinum based on the silver, and then dried at 100° C with mixing. The resulting dry powder was reduced by heating it in an atmosphere of hydrogen gas at 300° C. for an hour, followed by cooling, grinding and classification. This catalyst was called "catalyst O".

p) 50 g of supported catalyst L was impregnated with an aqueous solution of palladium nitrate containing 1.0 wt. % of palladium based on the silver, and then dried at 100° C. with mixing. The resulting dry powder was reduced by heating it in an atmosphere of hydrogen gas at 500° C. for an hour, followed by cooling, grinding and classification. This catalyst was called "catalyst P".

(Reaction)

Each of supported catalysts M–P was classified. Then, a stainless steel reactor having an inner diameter of 27.4 mm was packed with 5 ml of a fraction having particle sizes of 500 to 250 μm so as to form the lowermost catalyst layer. Then, 5 ml of a fraction having particle sizes of 250 to 150 μm was placed on the lowermost catalyst layer and, further, 5 ml of a fraction having particle sizes of 150 to 105 μm was placed as the uppermost catalyst layer.

To the reactor packed in the above-described manner were fed 1,2-propanediol containing trimethyl phosphite in an amount of 3 ppm, as phosphorus, based on the 1,2-propanediol at a rate of 140 g/hr, water at a rate of 140 g/hr, air at a rate of 220 liters/hr, and nitrogen at a rate of 400 liters/hr. These components were fed through an evaporator and a preheater so as to form a descending flow. After the reaction was continued for 10 days, the reaction gas was cooled and the product was collected by separation in an absorption column using water as absorbent. The results of the reactions are shown in Table 4.

COMPARATIVE EXAMPLES 6

The supported catalyst L was classified. Then, in the same manner as in Example 5, a reactor was packed with the supported catalyst and reaction was carried out. The results of the reactions are shown in Table 4.

COMPARATIVE EXAMPLE 7

A reactor was packed with each of supported catalysts M–P in the same manner as in Example 5. Then, reaction was carried out by passing a reaction gas through the reactor in the same manner as in Example 5, except that no phosphorus was added to the reaction gas. The results of the reactions are shown in Table 4.

TABLE 4

| | Reaction temperature (°C.) | Conversion of PG (%) | Selectivity for MGX (%) | Yield of acetol (%) | Space time yield (g/cm³ · hr) |
| --- | --- | --- | --- | --- | --- |
| Example 5 | | | | | |
| Catalyst M | 518 | 99.8 | 67.0 | 3.0 | 5.9 |
| Catalyst N | 512 | 99.7 | 65.8 | 2.5 | 5.8 |
| Catalyst O | 520 | 99.9 | 68.6 | 1.6 | 6.0 |
| Catalyst P | 515 | 99.8 | 68.8 | 1.7 | 6.0 |

TABLE 4-continued

| | Reaction temperature (°C.) | Conversion of PG (%) | Selectivity for MGX (%) | Yield of acetol (%) | Space time yield (g/cm³ · hr) |
| --- | --- | --- | --- | --- | --- |
| Comp. Ex. 6 | | | | | |
| Catalyst L | 518 | 99.7 | 59.4 | 7.1 | 5.2 |
| Comp. Ex. 7 | | | | | |
| Catalyst M | 525 | 99.9 | 56.7 | 3.1 | 4.3 |
| Catalyst N | 520 | 99.9 | 53.3 | 3.0 | 4.1 |
| Catalyst O | 527 | 99.9 | 57.0 | 2.2 | 4.2 |
| Catalyst P | 522 | 99.9 | 57.6 | 2.3 | 4.4 |

Note: PG and MGX represent 1,2-propanediol and methylglyoxal, respectively.

As is evident from Tables 1–4 above, the process of the present invention makes it possible to produce glyoxals in high yield while achieving a high conversion of the raw material and a high space time yield and while minimizing the formation of by-products.

What is claimed is:

1. A process for producing glyoxal which comprises conducting oxidative dehydrogenation of a glycol at a temperature of 400° to 700° C. in the presence of a silver-based catalyst and phosphorus or a phosphorus compound, wherein the silver-based catalyst is composed of i) silver particles coated partially with at least one element selected from the group consisting of gold, platinum, rhodium and palladium or ii) particles of a silver supporting inert carrier wherein at least one element selected from the group consisting of gold, platinum, rhodium and palladium is supported on the surface of the particles, and wherein the phosphorus or the phosphorus compound is mixed with the glycol prior to conducting said oxidative dehydrogenation or is added to the process separately from the glycol.

2. The process of claim 1 wherein the glycol is ethylene glycol or 1,2-propanediol and the glyoxal produced by the process is correspondingly glyoxal or methylglyoxal.

3. The process of claim 1 wherein the silver-based catalyst is reduced prior to conducting oxidative dehydrogenation.

4. The process of claim 1 wherein the phosphorus or phosphorus compound is added in an amount in the range of 0.05 to 10 ppm, as phosphorus, based on the glycol.

5. The process of claim 1 wherein the element is present in the silver-based catalyst in the range of 0.001 to 10 wt. % based on the silver.

6. The process of claim 1 wherein the element is present in the silver-based catalyst in the range of 0.001 to 10 wt. % based on the silver, the phosphorus or phosphorus compound is added in an amount in the range of 0.05 to 10 ppm, as phosphorus, based on the glycol, and the glycol is ethylene glycol or 1,2-propanediol and the glyoxal produced by the process is correspondingly glyoxal or methylglyoxal.

7. The process of claim 1 wherein the silver-based catalyst is composed of an inert carrier selected from the group consisting of silica, alumina, zirconia, silicon nitride and silicon carbide.

8. The process of claim 1 wherein the silver-based catalyst is composed of an inert carrier having a specific surface area of 0.01 to 5 m²/g and a particle diameter of 25 to 1,000 μm.

9. The process of claim 1 wherein the silver-based catalyst is ii) and the amount of silver supported is in the range of 50 to 95 wt. % based on the combined weight of the inert carrier and the silver supported thereon.

10. The process of claim 1 wherein the silver-based catalyst is ii) and the inert carrier has a specific surface area of 0.01 to 5 m²/g and a particle diameter of 25 to 1,000 μm, the amount of silver supported is in the range of 50 to 95 wt. % based on the combined weight of the inert carrier and the silver supported thereon, the phosphorus or phosphorus compound is added in an amount in the range of 0.05 to 10 ppm, as phosphorus, based on the glycol, and the glycol is ethylene glycol or 1,2-propanediol and the glyoxal produced by the process is correspondingly glyoxal or methyl-glyoxal.

* * * * *